(12) United States Patent
Nutting et al.

(10) Patent No.: US 8,076,924 B2
(45) Date of Patent: *Dec. 13, 2011

(54) SUBSTANCE IDENTIFICATION AND LOCATION METHOD AND SYSTEM

(76) Inventors: John Nutting, Edmonds, WA (US); Richard Daniel, Kingston, WA (US)

(\*) Notice: Subject to any disclaimer, the term of this patent is extended or adjusted under 35 U.S.C. 154(b) by 0 days.

This patent is subject to a terminal disclaimer.

(21) Appl. No.: 12/916,765

(22) Filed: Nov. 1, 2010

(65) Prior Publication Data

US 2011/0050241 A1    Mar. 3, 2011

Related U.S. Application Data

(63) Continuation of application No. 11/978,775, filed on Oct. 29, 2007, now Pat. No. 7,825,648.

(51) Int. Cl.
*G01N 27/00* (2006.01)

(52) U.S. Cl. .................. 324/71.1; 324/633; 324/637

(58) Field of Classification Search .............. 324/71.1, 324/637; 73/587, 589, 603, 604, 801
See application file for complete search history.

(56) References Cited

U.S. PATENT DOCUMENTS 7,825,648 B2 * 11/2010 Nutting et al. ............... 324/71.1

\* cited by examiner

*Primary Examiner* — Vincent Q Nguyen
(74) *Attorney, Agent, or Firm* — Dean A. Craine

(57) ABSTRACT

This invention relates to a method and system for remote detection of a targeted substance by the appropriate application of a probing signal that induces molecular resonance in the target substance to create an identifiable signature or response. In the preferred embodiment, signals transmitted are an Infrared laser beam, amplitude modulated in the range of 100 kHz frequency. The probing signal stimulates molecular resonance of the target substance which produces characteristic electron signal responses that are detected by IR detectors. A software program is used to process the electrical response signals and to compare them with electrical response signals stored in a database of known substances, thus allowing the target substance to be identified. The system may also be used to locate targeted substances. Also disclosed is an artificial ground device that provides a positive ground that provides consistent responses.

1 Claim, 10 Drawing Sheets

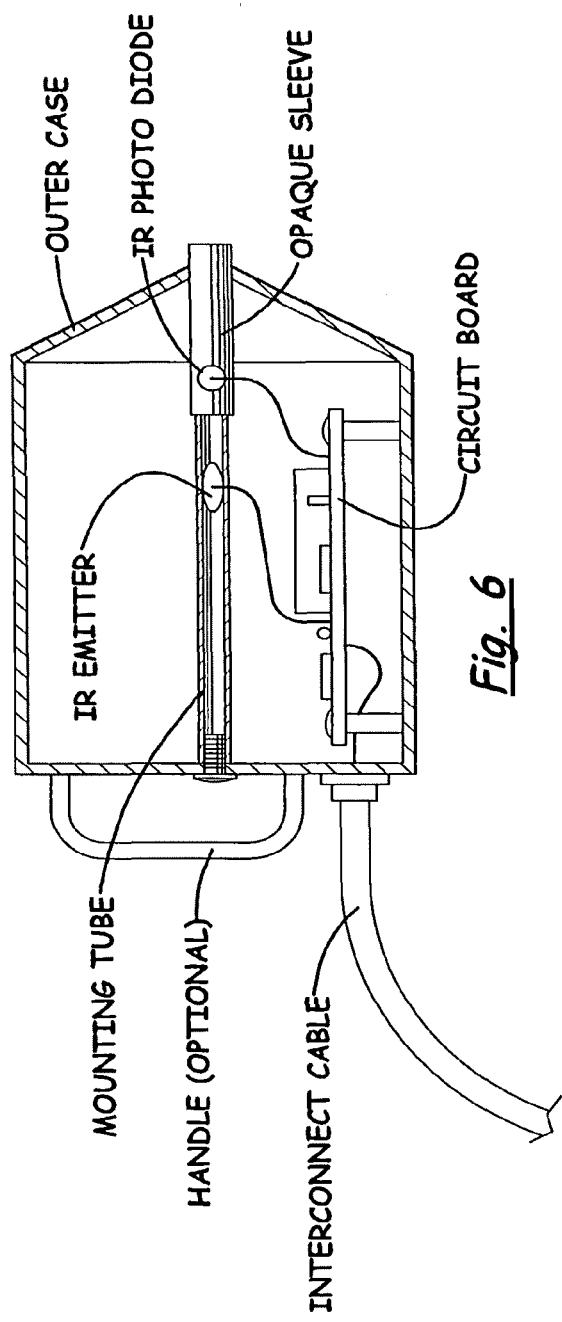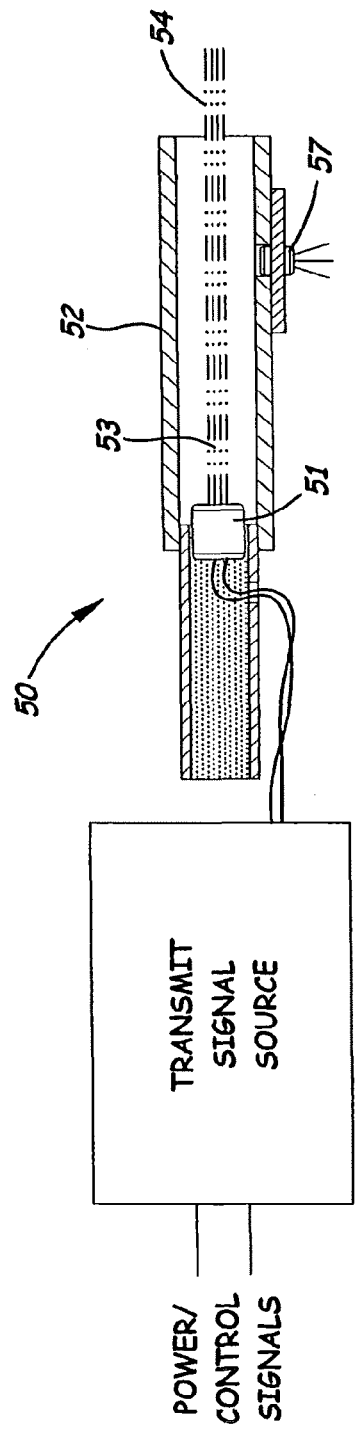

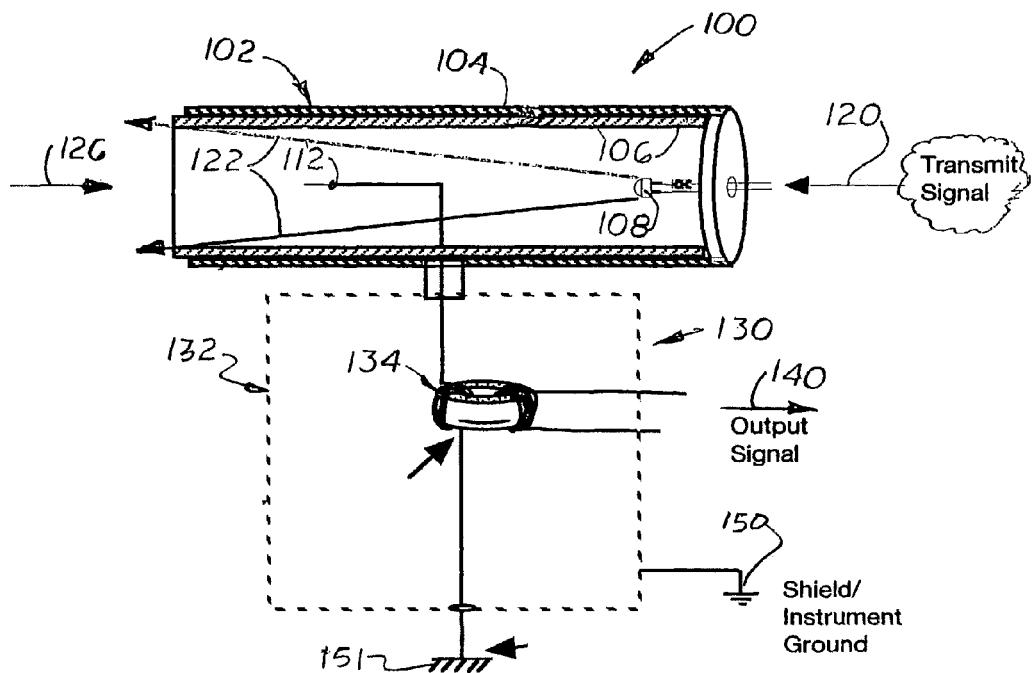
FIG. 12
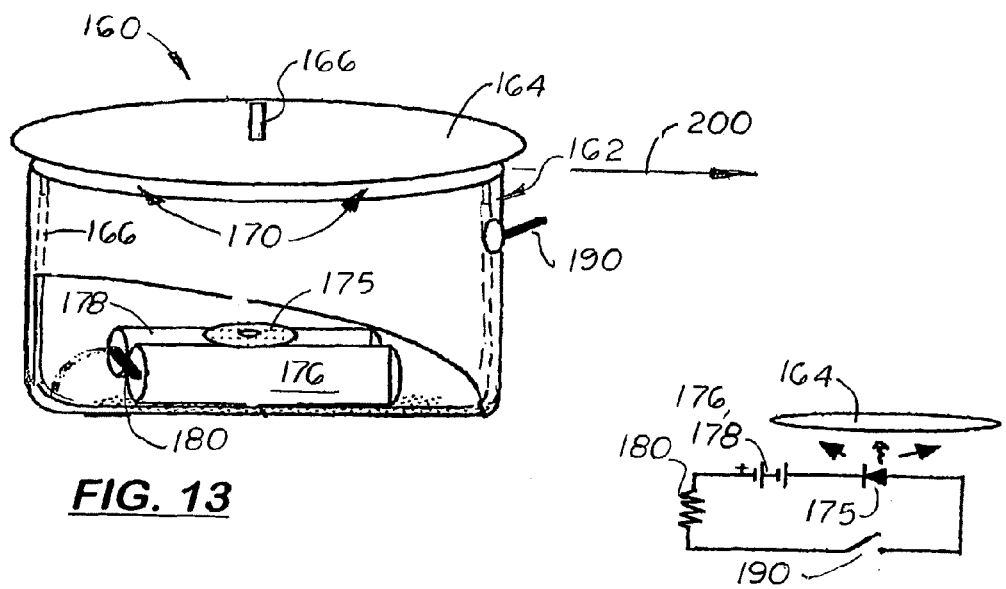
FIG. 13
FIG. 14

U.S. Pat. No. 8,076,924 B2

SUBSTANCE IDENTIFICATION AND LOCATION METHOD AND SYSTEM

This is a continuation application that claims priority to the continuation-in-part patent application (Ser. No. 11/978,775), filed on Oct. 29, 2007 which claimed priority to the utility patent application (Ser. No. 10/444,421), filed May 23, 2003.

BACKGROUND OF THE INVENTION

1. Field of the Invention

The present invention relates generally to methods and systems for determining the presence of a chemical element or compound, and more particularly, to such methods and systems that stimulate substances at selected frequencies of resonance, to produce characteristic patterns of emission that can be detected locally or from a remote distance to determine the identity and location of the substance.

2. Description of the Related Art

A number of patents have been issued that relate to techniques for relatively short-ranged location systems, and most are designed to find a particular class of substances. Typical of these are U.S. Pat. Nos. 5,159,617, and 5,233,200, issued to King et al., and Buess, et al., respectively. These patents typically relate to substances that contain Nitrogen, and generally use electromagnetic fields to disturb atomic structures, and measure the resulting emissions, as the atoms return to normal. Compared to the proposed method disclosed herein, these techniques are extremely limited, both in type of substances that can be detected, and in detection distance.

U.S. Pat. No. 3,050,627, issued to Miller, describes a method of detecting natural nuclear emissions, without stimulation of any kind. It appears that this patent may have been based upon observations of the same, or similar, natural phenomena that are the basis of this invention, but with a different technological focus, and in an entirely different frequency band. It should be noted that the patent was issued in 1962, and has expired without major development, which indicates a lack of fulfillment of expectations. The inventors have found that substances may emit noise signals, as Miller suggests, however, they do so in response to a stimulating energy source, whether natural, or artificial, so that the laws of thermodynamics are not violated. Means of stimulating substances artificially are part of the present invention. Also, it has been found, by the present inventors, that substance emitted noise signals require interpretation in order to be useful for substance identification. Means to interpret substance generated noise is also an important part of this invention.

SUMMARY OF THE INVENTION

It is an object of the present invention to provide a method and system for identifying and locating a targeted substance either locally or remotely.

It is another object of the present invention to provide such a method and system that does not destroy or damage the targeted substance.

These and other objects of the present invention are met by a remote substance identification and location method and system disclosed herein that uses an ionization means used to ionize an intermediate chemical to produce a probing signal, also called a plasma, used to simulate and sense the response from a desired substance located in a target area. The intermediate chemical can be any chemical that undergoes ionization caused by an IR laser beam source. The embodiment disclosed herein is used in an open area exposed to the atmosphere where the intermediate chemical is oxygen, or nitrogen. During use, the probing stimulating signal is aimed at or in the general direction of a desired target substance causing the target substance to undergo non-destructive molecular resonance to produce a characteristic electrical response field. The electrical response signal is then detected by IR detectors tuned to the same electromagnetic band as the intermediate chemical. The IR detectors are connected to a preamp and an analog/digital converter which interfaces with a computer. Loaded into the memory of the computer is a software program that is programmed with a library of electrical response signals from known target substances using a calibration method a first algorithm. The software program includes a second algorithm that compares the received electrical response signals to electrical response signals from known substances to determine the identity and location of the target substance.

In the preferred embodiment, the intermediate chemical is oxygen which is ionized by the IR laser beam source to create a single pulse-modulated plasma that causes molecular resonance in the target substance.

In one embodiment, the ionization means is an optical radiation source, such as an IR laser beam source. In another embodiment, the ionization means is a voltage radiation source, such as an antenna.

In another embodiment, metallic and insulative shields are provided that reduce noise signal responses.

DESCRIPTION OF THE DRAWINGS

FIG. 6 is a sectional, side elevation view of a plasma detector used in the system.

FIG. 7 is a diagram of an optical based laser beam generator.

FIG. 12 is a diagram of another embodiment of the invention for stimulating a response signal from target substance that includes metallic and insulative shields that reduce noise interference.

FIG. 13 is an illustration of an artificial ground used with the embodiment shown in FIG. 12.

FIG. 14 is a schematic diagram showing of the artificial ground shown in FIG. 13.

DESCRIPTION OF THE PREFERRED EMBODIMENT(S)

Figure 1:
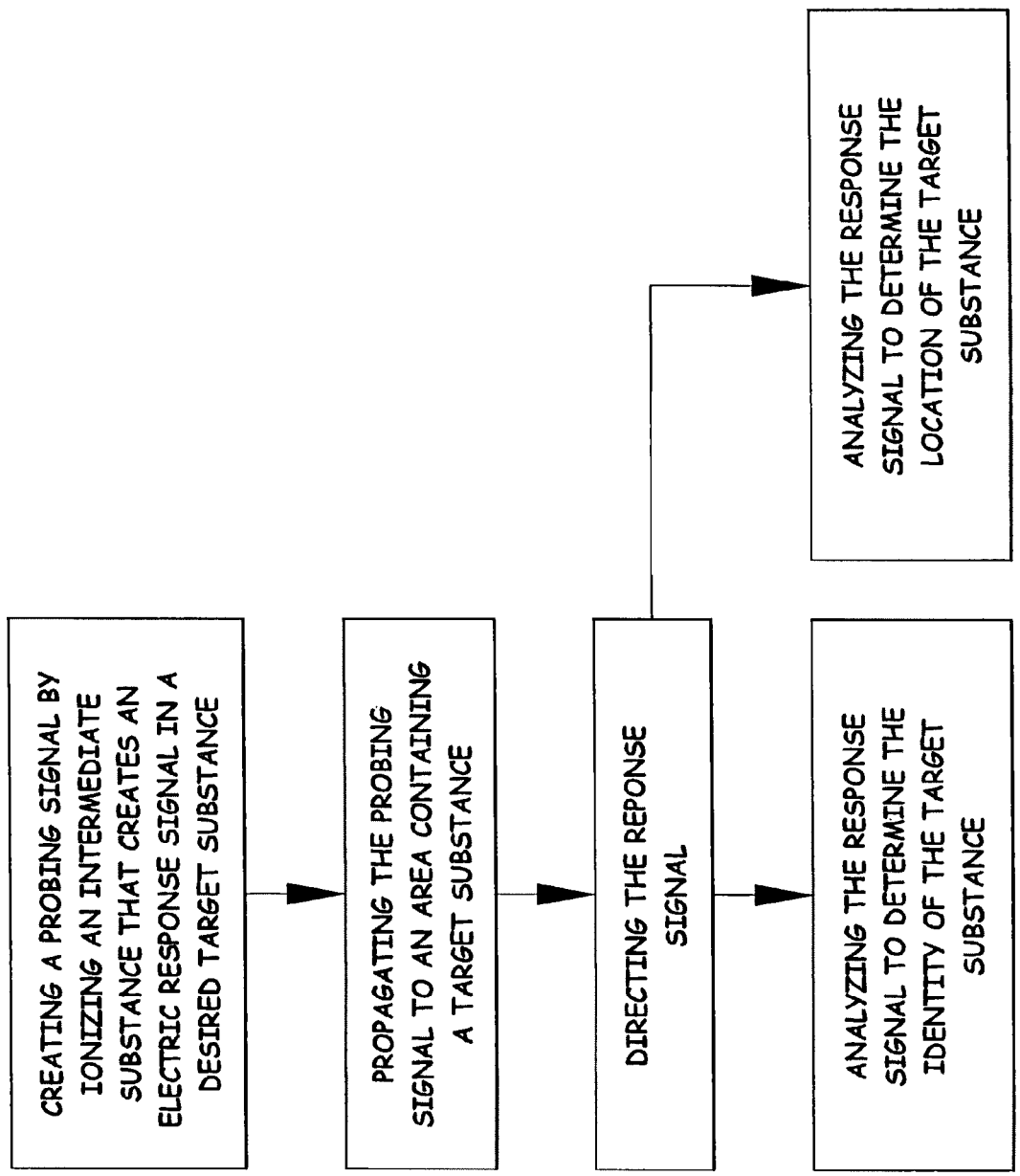
FIG. 1 is a simple block diagram of the method used for remote substance identification and location.
Figure 2:
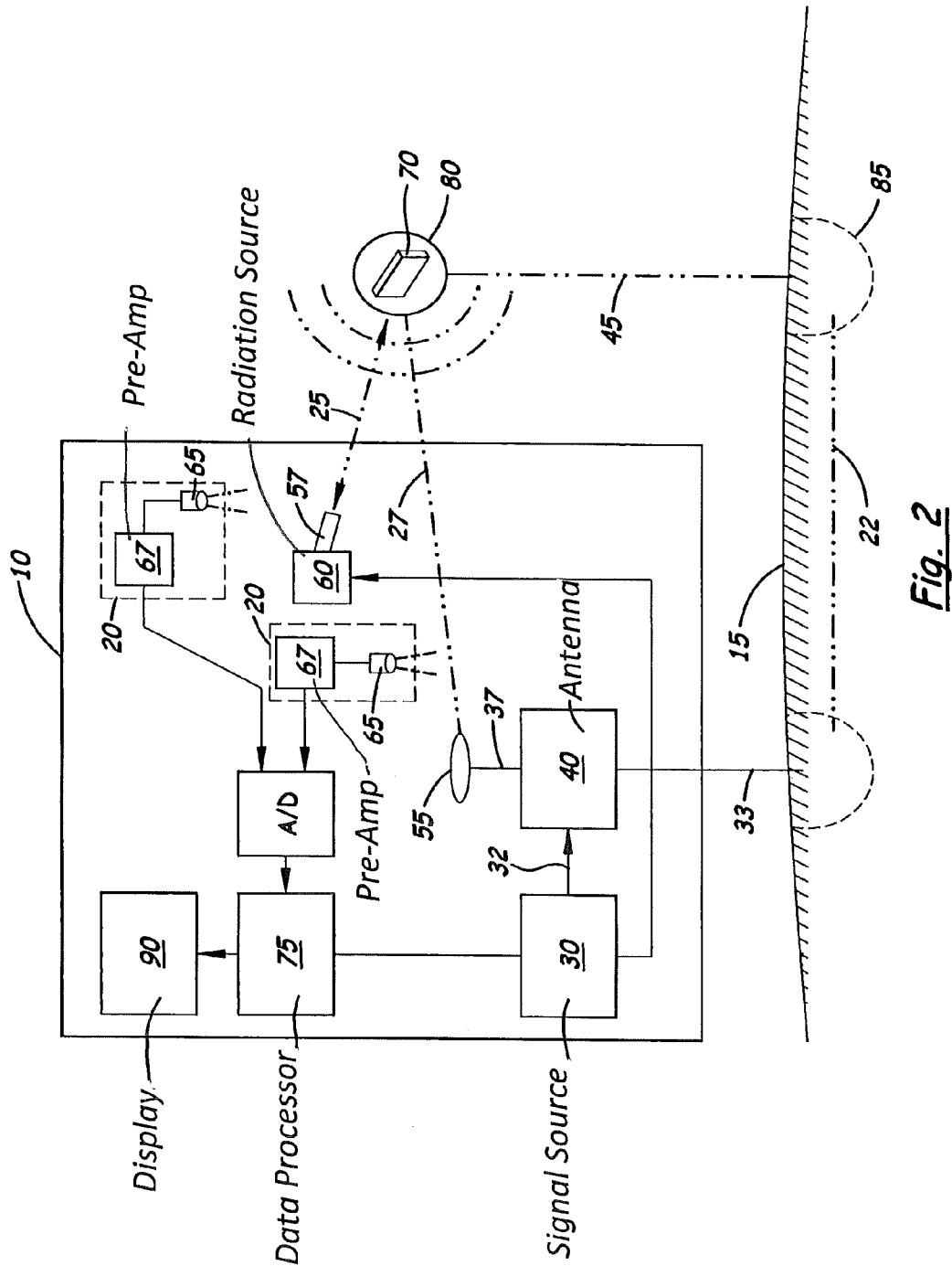
FIG. 2 is a diagram of the substance identification and location system disclosed depicting the use of both an omni-directional voltage radiation source and a uni-directional optical radiation source.
Figure 3:
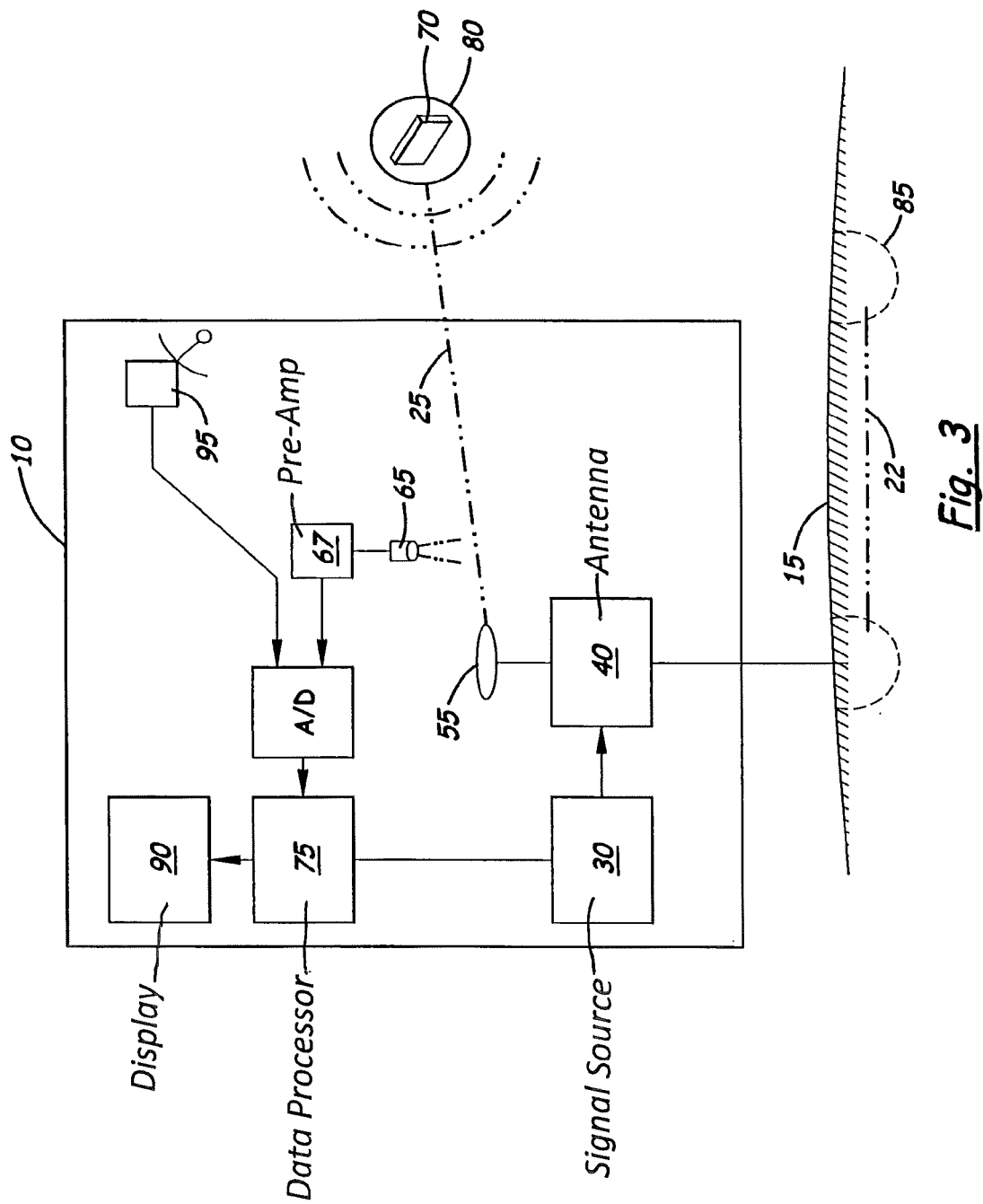
FIG. 3 is a diagram of the remote substance identification and location system disclosed herein depicting the use of an omni-directional voltage radiation source and a remotely operated electric field detector.
Figure 4:
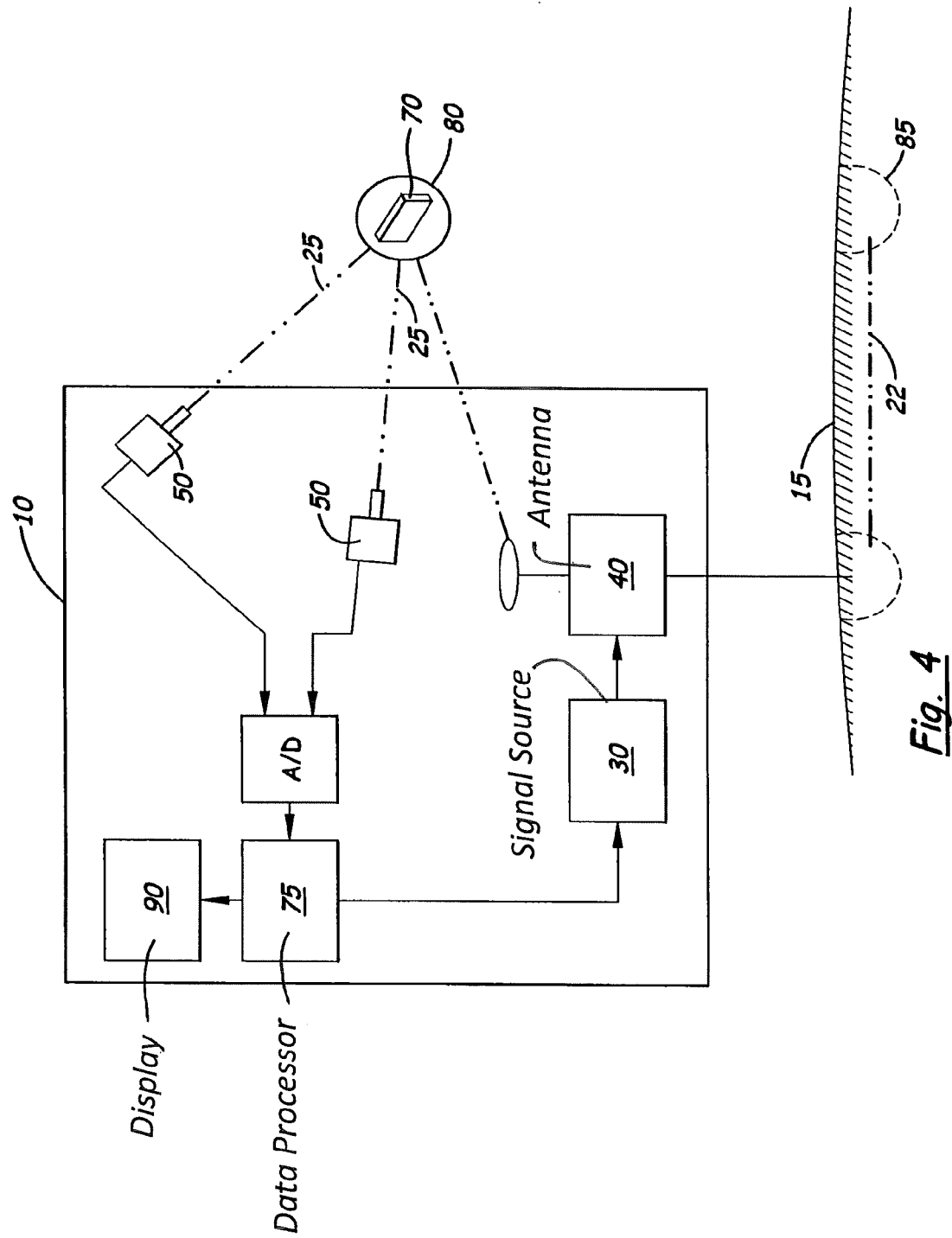
FIG. 4 is a diagram of the remote substance identification and location system that depicting the use of an omni-directional antenna that produces a probing signal and two plasma detectors that detect an electric stimulating signal.
Figure 5:
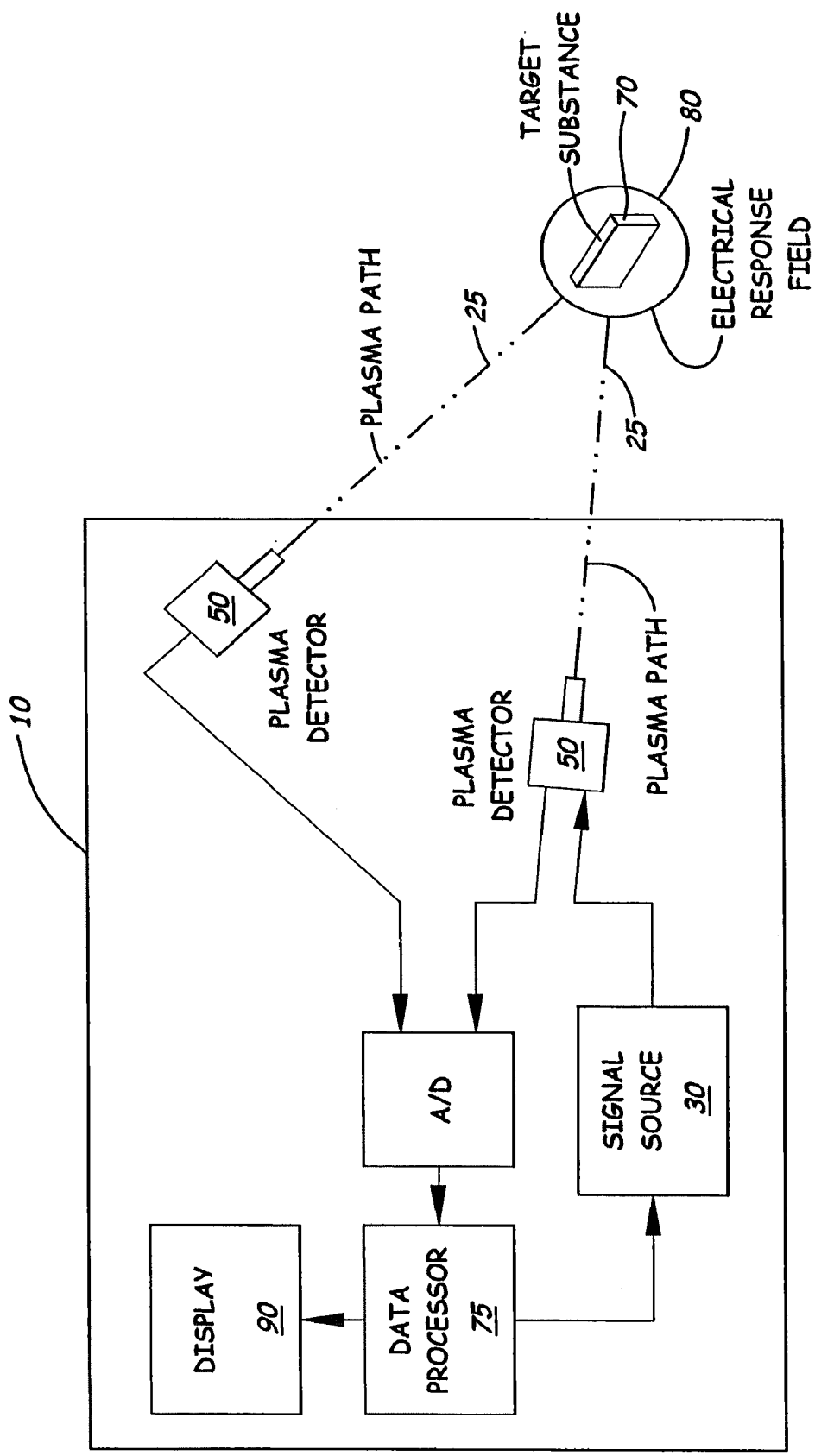
FIG. 5 is a diagram of a remote substance identification and location system that used two plasma detectors both used to create probing signals and to detect an electric stimulating signal.
Figure 9:
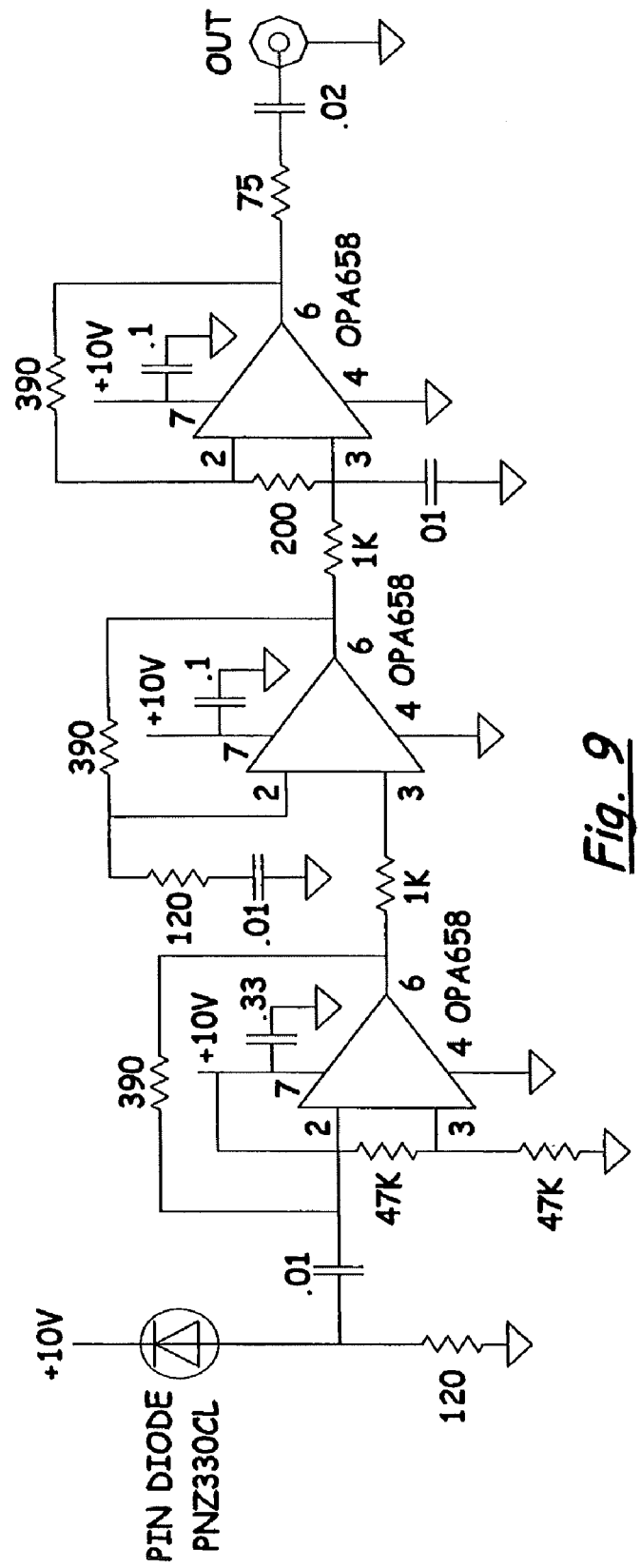
FIG. 9 is a schematic diagram of a wide-band sensor, and pre-amplifier used with the system shown in FIG. 6.
Figure 10:
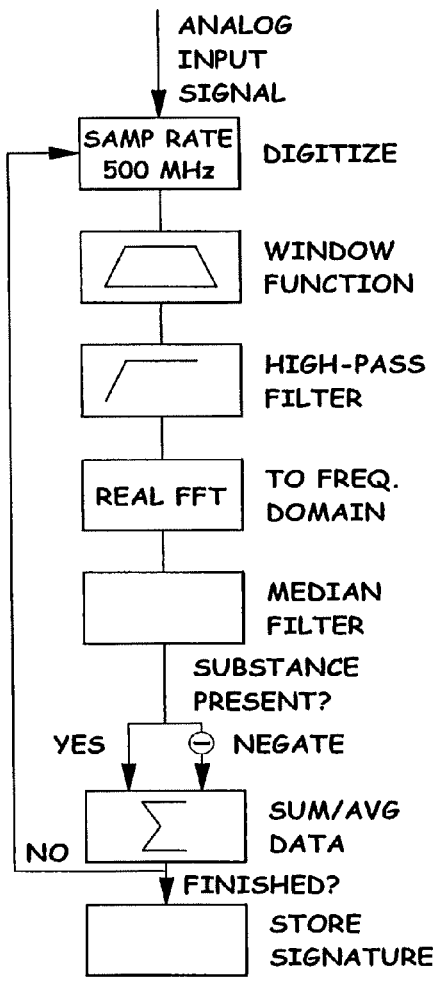
FIG. 10 is a flow diagram of the data processing algorithm used by the remote substance system for determining the substance signature of a known target substance.
Figure 11:
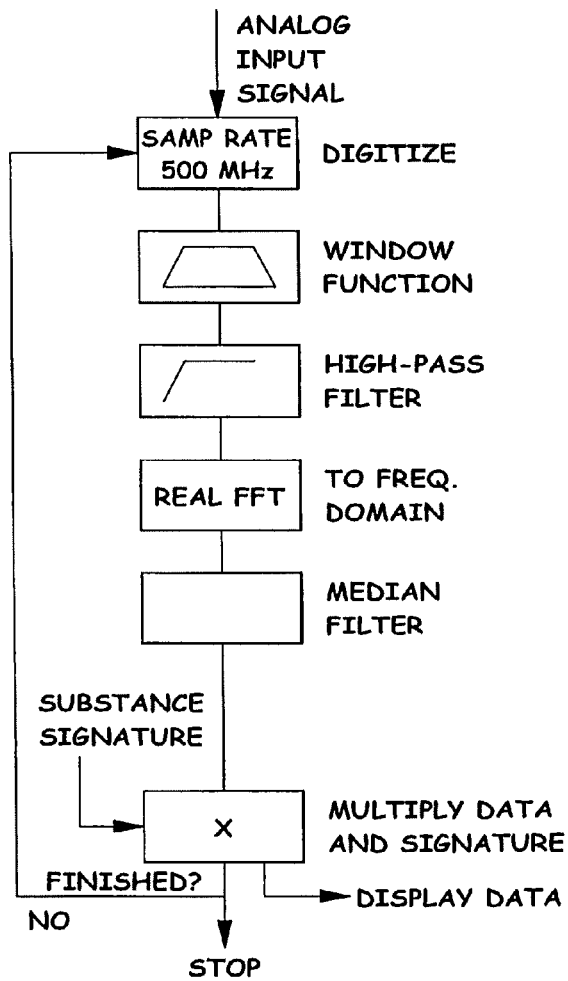
FIG. 11 is a flow diagram of the data processing algorithm used by the remote substance identification system for determining the location of a target substance.

Disclosed herein and depicted in the accompanying Figs. is a remote substance identification and location method and system 10 also referred to as Object Location by Electrical Response (OLER). The method, depicted generally in FIG. 1, includes a first step of creating a probing signal by ionizing an intermediate substance, propagating the probing signal to the area containing a target substance 70 which creates an electrical response field from the target substance, detecting the electrical response field from the target substance 70, and then analyzing the electrical response field to identify, and locate the target substance 70. FIG. 2 depicts an overall summary of the system 10 while FIGS. 3-5 depict three specific design applications of the system. FIGS. 6-9 are illustrations and schematic diagrams showing two types of plasma generators used in the system 10 while FIGS. 10 and 11 are flow diagrams of two software algorithms used by the system 10. FIG. 12 is a diagram of another embodiment of the invention for stimulating a response signal from target substance that includes metallic and insulative shields that reduce noise interference. FIGS. 13 and 14 are diagrams and schematics, respectively, of an artificial ground used with the embodiment shown in FIG. 12.

Remote identification and location of arbitrary molecular substances has long been a goal of many inventors, but has generally gone unfulfilled. Standard substance identification methods include laboratory techniques, such as Nuclear Magnetic Resonance, and Optical Spectrometry, but these methods provide no means of identifying substances in field conditions, except in astronomy, nor do they have distant location capability. The technique known as X-Ray Fluorescence (XRF) is being used in field work to find and measure certain substances, but the maximum range of XRF operation is a few inches, so it is not capable of remote monitoring, and is severely limited by range in locating objects. Other techniques that have been used include, x-ray, and acoustic means to measure density of a substance, and means of measuring earth conductivity anomalies, for buried objects. Probably the best method to date for locating certain substances is the animal sense of smell, but this method is obviously limited to substances that provide a smell.

The advantages of the system 10 disclosed herein over other systems found in the prior art is the ability to locate small or large amounts of target substances at different distances While some substances, of course, are stronger signal sources than others, the system 10 may be adjusted to identify and locate a wide variety of different target substances. For example, gasoline is considered a relatively strong target source, and a tank of gasoline in an automobile can be detected a city block away. A tank-farm of gasoline can be detected more than 3 miles away.

The system 10 also offers a method of finding people buried in avalanches, and rubble, even finding dead bodies, and could be used in police searches for weapons, bombs, and narcotics. It could be used in mining to locate precious metals, and gems, though the technique may not penetrate deeply into the soil, and tests of soil penetration have not yet been made. The potential list of uses is long. Obvious important uses of the system 10 include means to alert security persons to presence of plastic explosives that are extremely difficult to detect by other means.

Another advantage of the system 10 is its inherent safety. Detection methods do not require hazardous materials, such as nuclear sources, or other dangerous radiation. The electromagnetic radiation associated with the system 10 is hardly more than a person experiences when walking across a carpet, and much less than one gets standing in sunlight.

Stimulation of a Target Substance

It is postulated that most, if not all, substances generate characteristic electrical response signals when stimulated with a "proper" electrical signal. These response signals, are low in frequency, and are electrically weak, which is to say that their source impedance is extremely high even though their voltage levels may be moderate to high. Actual values are difficult to measure, and are not yet known, because an adequate model has not been built. Response signals have been found in the frequency band from nearly DC to approximately 200 MHz. It is anticipated that that frequency may be a limitation of the present instrumentation, rather than of the substances, or the propagation medium.

The system 10 uses a probing signal to simulate and sense a response from a desired substance located in a target area. The probing signal is produced by an ionization means that ionizes an intermediate chemical that is propagate, stimulate, and sense the target area. In the preferred embodiment, the intermediate chemical undergoes ionization caused by an IR laser beam source. It is postulated that the probing signal causes the resonance in the electron clouds in the molecules of the intermediate substance. It is accepted that all substances consist of combinations of atoms held together with shared electrons, commonly called valence electrons. In his book, The Nature of the Chemical Bond, Linus Pauling, explored the wave-like nature of electrons, and showed how in chemical bonds, electrons form a stable waveform when considered as a mutual resonance of two waveforms. Now, electrons are charged particles, so it follows that they can be moved (attracted, or repelled) by electric fields, and if the frequency of an alternating E field is adjusted, suitably, the resonant chemical bond will vibrate and eventually break causing an electron to be ejected, like a stone from a sling. The 'Q' of the resonance is unknown, but it likely is quite large, because a very small amount of energy, added over a relatively long time period, can create the effect. Moreover, resonances can be stimulated using one of many sub-harmonics. So, it follows that extremely low frequencies can be used to stimulate substances. Characteristic substance stimulation frequencies have been observed to be relatively stable over time as compared to response signal signatures (see section on Detection).

Natural electrical noise can also stimulate these emissions, particularly on sunny days. The system-like signatures found in many substances may be observed during daytime hours without artificial stimulation. It has also been observed that some substances can be stimulated at, or near, harmonics of 60 Hz, when located near power lines.

Propagation

In the preferred embodiment disclosed herein, the propagation of the probing signal and the electrical response signal from the target substance takes place in air with a return current path through the earth, but not necessarily. Wherein, due to natural presence of air atoms with orbital electrons, and ions, electrical response signals generated at one location can be transmitted through the ion/air "fluid" by physical shift, or vibration, of electrons, or ion particles, as described in plasma physics. This effect is similar to well known principles of acoustics, substituting electric field force for mechanical pressure. Like acoustics, the propagation medium is subject to ducting, that is, the formation of low-loss paths, such as the propagation of sound across a lake. Lonngren, author of "Introduction to Physical Elements", generally describes ion acoustic waves having properties similar to those observed by the inventors, and it is expected that this propagation mode is a plasma physics phenomenon, perhaps like the Ion Acoustic Wave, but using the vibration of orbital electrons of air molecules, because light electrons would provide a higher propagation velocity, and response frequency than would heavier ions.

Unlike ordinary acoustics, the ions that provide the propagation are physically moved to generate plasma paths. This may be accomplished by either of two methods: an application of light at emission wavelengths of Oxygen (e.g. 820 nm), as published in the Handbook of Chemistry and Physics; or a simple grounded sharp pointed conductor will often work, particularly when ambient sunlight is present. Creation of a plasma path also requires application of an electric field that has a frequency that is very near to a resonant frequency of the substance being sought. The two signals, (stimulus and response) with a slowly varying phase relationship, create an effect like electrically polarized electrodes in a conductive fluid. When a plasma path is created, a minute current flows, and follows a path of least impedance between the stimulated substance and the transmitter. This may be a direct line, but will not always be so. If the path of least resistance passes through a wall, the laws of dielectrics apply, and refraction may occur, changing the apparent direction of the path. In fact, the path may split into two, as has been observed, where one path can go directly through a door, and another through an air space beside the door, simultaneously. In a preferred embodiment, an infrared (IR) laser is used to trigger a stimulating plasma path, stimulate the target substance, and detect the electrical response, all in a single instrument.

Additional theoretical work has been done to better understand the propagation phenomenon in terms of quantum physics. A simplified explanation likens the air molecules to tiny energy-wells, physically separated in space. IR energy, such as sunlight, partially fills the wells making it easy for energy from a source, such as stimulated substance molecules, to travel in any direction, depending upon the potential gradient, like balls on the slope of a tilted surface.

Detection of the Electrical Response Signal

Once a path, or duct, has been set-up using the electrical fields generated by the transmitter, and its associated antenna, it is possible to detect the electric response signals using one of several types of sensors designed for that purpose. In the preferred embodiment, an infrared (IR) laser beam source is used that emits in the IR band of 820 nm caused by oxygen molecules in the air. The electrical response signals from the target substance are narrow pulses emitted from the orbital electrons of the oxygen molecules as they pass charges along the 'path', and are particularly strong in the vicinity of the transmit antenna element, where the current is most concentrated. The IR detector integrates the pulses forming an analog of the current that passes along the path. Detection is most sensitive, if the IR detector is mounted at a right-angle to the path, but not inside the path.

The currents that flow are generated by electrical actions of orbital valence electrons, as they continually seek a stable relationship with themselves and with the disrupting influences of external fields. It should be understood that other sensors may be used to detect these fields, including electric, and magnetic field sensors, to detect the target substance by its stimulated noise field, or to detect the path by its electromagnetic noise field. For example, some of these noise field sensors have been built, and used with degrees of success, however they tend to suffer from electrical isolation problems that the IR current sensors do not, because of inherent isolation by optical coupling. The only problems experienced with the IR detectors are sensitivity to sunlight, and to 60 Hz interference related to incandescent lighting. These problems may be solved using differential sensors, or by placing the sensors inside of opaque housings.

Signals can also be optically detected directly, using an Infrared (IR) detector of a suitable sensitive wave-length, 823 nm is ideal. Ionized paths create an IR 'glow' that can be detected by looking directly in the direction of a substance, after a 'path' has been set-up. This glow may be observed on the ground above, or near, location of the buried object(s). This type of detection may be useful for certain applications, but may suffer from solar noise problems. Implementation of this detection method is similar in design to that described herein, but using the IR diode sensor directed toward the suspected location of the 'glow.' It may also be practical to build a device that will allow the human eye to observe the 'glow'.

Figure 8:
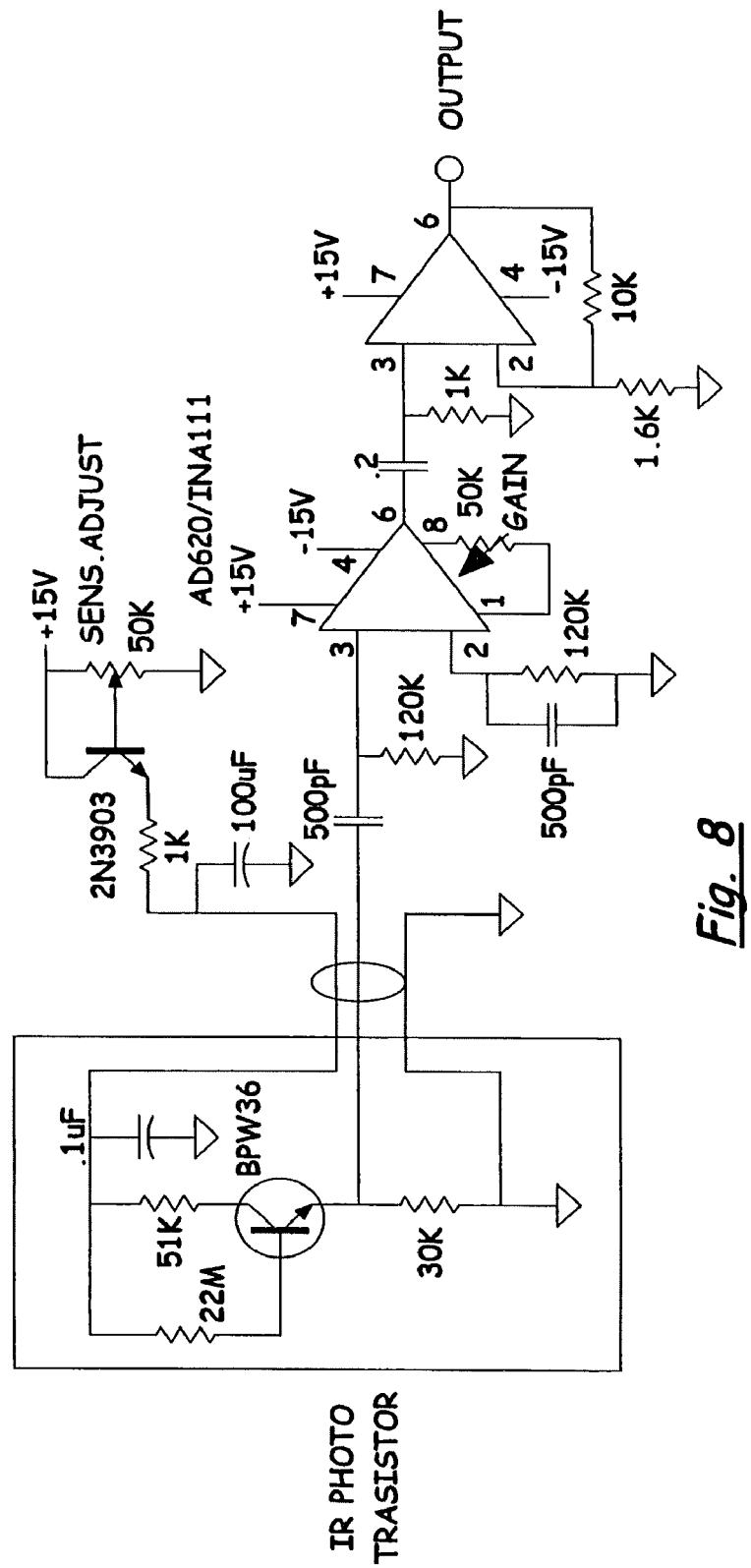
FIG. 8 is a combination schematic of the plasma detector and probe beam generator shown in FIGS. 6 and 7.

FIG. 8 shows a typical plasma sensor mechanical construction, with a schematic diagram of a sensor, and a preamplifier, which operates in the acoustic frequency band (up to 100 kHz). FIG. 9 shows a schematic diagram of a wide-band sensor (up to 250 MHz). The PIN Diode shown in FIG. 9 replaces the IR photo-transistor shown in FIG. 8.

FIG. 12 shows an alternative embodiment of the IR detector 100 designed to reduce the noise signal response. The detector 100 includes a cylindrical outer housing made of a metallic outer shield 104 and a coaxially aligned, insulative inner shield Using this embodiment, stimulation occurs by infrared radiation, modulated by a transmit signal 120 which drives one or more infrared emitters 108 located inside the outer housing 102. In the preferred embodiment, the outer housing 104 is made of metal while the inner shield 106 is made of plastic, (PVC). During operation, the infrared emitter 102 produces a beam of IR radiation 122 which is broadcast outward through the open end of the outer housing 102. The modulated IR then stimulates a response signal 126 by the target substance which is detected by the electrode 112 located inside the outer housing 102. The electrode 112 is electrically connected to transformer assembly 130.

The transformer assembly 130 includes a metallic outer housing 132 with a wide band transformer 134 located therein that connects to the electrode 112. During operation, the transformer 134 amplifies and produces an output signal 140. In the preferred embodiment, the turns-ratio of the transformer 134 is a 1:2 step up which provides a gain factor of 2. It should be understood however, that other turns ratios maybe used.

In order to reduce the noise signal responses, the electrode 112 must be shield by the two metallic shields 104 and 132 in the outer housing 102 and transformer assembly 130, respectively and by the insulative shield 106 in the outer housing 102. A separate ground connection 150 for the shields 104, 106, and 132 and the input and output signals 120, 140, respectively, are necessary to eliminate noise interference.

To obtain consistent responses from the OLER system, positive grounding is also necessary. It has been observed, however, that all grounds are not consistent. A useful solution is to provide an artificial ground device 160 as shown in FIGS. 13 and 14.

Referring to FIG. 13, the artificial ground device 160, also known as an AGD 160, that includes a closed, hollow outer housing 162 with a flat top lid 164. Attached to the lid 164 is a ground port connector 166. In the preferred embodiment, the outer housing 162 is made of transparent, insulative material. Located inside the outer housing 162 is an opaque, insulative shield 166. The insulative shield 166 is slightly smaller than the outer housing 162 and slightly small in height than the outer housing 162. A gap 170 is formed between the top edge of the insulative shield 170 and the inside surface of the top lid 164.

Located inside the outer housing 162 and inside the insulative shield 166 is an infrared emitter diode 175 that connects to one or more batteries 176, 178. The batteries 176, 178 are connected to a current limiting resistor (180) and to an optional ON-OFF switch (190. During operation, a connection is supplied from the instrument ground 151 shown in FIG. 12 to the ground port connector 166. The ON-OFF switch 190 is connected to the infrared diode 175 to produce an infrared signal 200 that is transmitted evenly inside the outer housing 162. Because a gap 170 is formed under the top lid 164, the infrared signal 200 is able to escape through the gap 170 and ionize the air surround the outer housing 162.

The AGD device 160 is typically placed on the surface or floor, at least one (1) meter below the sensor 100, which during operation provides a connection for the return path from the stimulated substance to the sensor. The combination of sharp metal points and IR radiation tends to ionize the air around the AGD device 160 and when energy is release by substance stimulation, current flows in the return path through the air, if earth ground is not available.

FIG. 14 is an electrical diagram showing the transmission of the IR signal through the window in the outer housing of the AGD device 160.

Signal Interpretation, and Calibration

The electric response signals emitted from target substances require interpretation before they can be used to identify and locate the target substance. The electrical response signal, without interpretation, appears generally as random noise. This is partly because the signals are themselves responses to random noise inputs. A novel feature of the invention is the algorithm disclosed below for interpreting the electrical response signals of target substance molecules.

Substances generally have a finite set of electron energy 'states', many of which are not stable. When disturbed by a transient field, the substance responds by executing a pattern of energy jumps, until equilibrium is reached. By quantum electronic theory, this activity involves only that set of energy states, but does not always involve them all. Identification of target substances, using this method, involves a signal processing algorithm that interprets substance noise as electron state activity, and includes a technique for measuring the characteristic responses of a target substance. This can be done under various conditions, to develop a reference signature which can be used as a match-filter to recognize signals from the target substance.

The first algorithm processes noise-like signals into characteristic patterns that are used to identify substances. As depicted in FIG. 10, the first algorithm uses a Fast Forier Transform (FFT), of a digitized signal, and performs a sequence of mathematical manipulations to produce a "signature" for the target substance. The signature is a spectrum-like table of responses averaged over variables of time, temperature, stimulations, etc. During the detection step, which is used in a second algorithm and shown in FIG. 11, the substance signature created during the search, is compared with similarly processed raw data received from the sensors. The comparison process produces a series of magnitudes that represent a likelihood that signals from a target substance are present.

An important aspect of the system 10 is the determination of the signature signal from a target substance. One method used to determine the signature signal is to measure and compare the changes in the electrical responses with and without the target substance in the target field. By subtracting the electrical response taken without the target substance from the electrical responses taken with the target substance, the actual electrical response from the target may be ascertained.

Another possible method used to determine the electrical signature of a target substance is to use a calibration chamber. A calibration chamber is made of a high-strength dielectric, such as glass, that completely surrounds the substance sample. A single conductor is used that allows an Infrared detector to monitor current flowing through a path-of-least-impedance. The substance sample may be stimulated with electrical fields, or by modulated infrared light, which is the preferred method used herein. The act of calibration involves a sequence of measurements whereby the substance's signature is determined.

Substance "signatures", as defined in this disclosure, are of two types, 1) Transmit Frequencies that cause resonant responses in substances, and 2) characteristic emissions, of electrical signals, from substances when they are stimulated at a frequency of resonance. The first type of signature is discussed in the above paragraph titled "Stimulation". The second type is discussed in the following paragraphs.

Experimental work has shown that substance, Type 2, signatures may change over time. Work remains to determine what parameters cause the observed changes, but theoretical considerations make temperature, and barometric pressure, to be suspects. Other possibilities include the concentrations of various gasses in the air-mixture, such as oxygen, nitrogen, and carbon dioxide. In a worst-case scenario, it may be necessary to do periodic in-situ calibrations using a known sample of the target substance.

Recent work with the high-frequency techniques have resulted in a simplified detection algorithm, due partly to better separation of substance response frequencies. The changed algorithm Flow Diagrams are shown in FIGS. 8 and 9.

Range Estimator Algorithm

A further novel algorithm is also provided for estimating the distance to the target. The algorithm complements the natural ability of the system to determine the direction of a substance by peak signal level, providing both range and bearing information, thus eliminating the need for two-sensor triangulation.

The algorithm is similar to a RADAR system (i.e. uses the transmission of a burst signal which is returned quickly if the target is near or later if the target is further away). The OLER signals, however, propagate slower that RADAR signal. Storage of data samples to scan for a 'match' with a stored signature is computer intensive for long ranges. The method was successfully tests, and provided satisfactory results at short distances. At long distances, however, a 'range gated' technique may be better (i.e. transmission of a pulse and waiting for a range-calibrated time period before beginning to digitalize the in-coming data). A combination of the two techniques might be used. In practice, it should be empathized that the system can operate in Omni Mode, where no range information is desired. It might be preferred for some applications to 'acquire' a target in that mode, then switch to the Range-Data mode, to determine its distance.

System Considerations

For some requirements it may be desirable to have a fixed omni-directional receiver antenna. For those applications, a receiver can be combined into the transmitter in such a way that any path that sets-up will be detected by the presence of a characteristic current flowing in the transmit antenna feed circuit. It will be possible to design such a system to continually monitor for the presence of any given substance, and provide warning signals when such presence is detected. A possible scenario could be to transmit multiple stimulation signals, and monitor for the response signal(s), that indicate the presence of selected target substances. Automatic location of an intruding target substance is possible with increased complexity.

Operation Description

FIG. 2 depicts a first embodiment of the system 10 that uses two receivers 20 that determine the target substance location by triangulation. An operator first selects a stimulus frequency, based upon the signature signal analysis of the target substance 70 to be located, and adjusts signal source 30 to provide an IR signal 32 of the desired modulated frequency and amplitude. The IR signal is transmitted by a voltage radiation source such as an antenna 40 or to an optical radiation source 60, such as an ionizing IR laser beam source. Upon activation of the antenna 55, or optical radiation source 60, a probing signal 25 is produced that stimulates the target substance 70 and causes it to generate an electrical response field 80. The electrical response field 80 causes a local disturbance field 85 in the earth ground 15 by electric induction, that is opposite in phase to the electrical response field 80, thus creating a local disturbance field 85. The electrical response field 80 and the local disturbance field 85 thus effectively create a dipole antenna. Two ion-plasmas 25 and 27 are formed that generate two signal paths, so that currents flow through the air 96 to the transmitter terminal 55. Note that the impedance of the Earth's soil is orders of magnitude lower than the impedance of the air propagation medium, so that ground impedance losses from the ground current 22 may be neglected. Transmit elements 33, and 37 (not shown in FIG. 2) provide ground return connections, so that current loops are completed back to the target substance 70. This atmospheric current proceeds as charges are passed from molecule, to molecule. Each transfer creates a pulse at Infra Red wavelengths, producing signals which may be sensed by two IR detectors 65. The two IR detectors 65 are connected to a preamp 67 that amplifies the signals and digitalizes them for further processing by a data processor 75. The first processing algorithm 66, shown in FIG. 10, is used to detect the signature signals that are shown to the operator on display 90.

A second embodiment of the system 10' is shown in FIG. 3. Several means exist of instrumenting the OLER effect, so that multiple options exist for optimizing a system design. FIG. 2 shows a system 10 that senses two ion plasma paths 25, 27, and determines the position of a target substance 70 by remote triangulation. In FIG. 3, a single plasma path 25 and an electrical field detector 95 are used. Such a system 10' might be used with a portable electrical field sensor 95, and a fixed plasma-path sensor, not shown. The plasma detector (not shown) could sense the direction of the substance, and the combination of the two sensors could be used to guide an operator to the exact location. The propagation velocity for the electrical field is much faster (light speed) than the plasma path (acoustic velocity), so a delay/correlation technique might be used to determine the approximate range of the target substance.

A third embodiment of the system 10" is depicted in FIG. 4 that includes two plasma detectors 50, 50' that are also used together to determine target position by means of triangulation. The system 10" can be used with, or without, a stimulation transmitter, which is useful if searches must be conducted at night. Hardware configuration of such a system 10", without transmitter, is shown in FIG. 5. The plasma detectors 50 may be hand-held, or tripod mounted. A typical mechanical configuration of a plasma detector 50 is shown in FIG. 6, with a circuit diagram depicted in FIGS. 7 and 8.

As shown in FIG. 7, the plasma detector 50 includes an infrared (IR) diode 51 mounted in a short tube 52 made preferably of stainless steel, or copper. The infrared light diode 51 produces IR light that ionizes oxygen molecules 53 inside the tube 52, generating a conductive plasma 54 within, and in front of the tubing. The tube 52 is electrically connected to a ground, or usable substitute such as the human body. This plasma 54 acts to provide a terminal for connecting to substance signals, much like a metallic terminal in a conductive fluid, except that the plasma is directional. When potentials are present, currents flow, and in the plasma as currents flow, pulses of IR light are emitted. These pulses are detected by the photo-transistor 57, mounted on the distal end of the tube 52 at a right-angle to the plasma 54. FIG. 8 is an electrical schematic of the plasma detector 50. The photo-transistor 57 has a sensitivity that peaks in the IR range, according to the emission spectrum of Oxygen (822 nm is ideal). The photo-transistor 57, in its circuit, detects the quasi-noise signals of stimulated substances in the pointing direction of the plasma probe. The signals are amplified, and passed to the analog to digital Computer interface, where signals are processed as described in the section on signal interpretation. Display can be as simple as meter deflections, or as sophisticated as an intensity vs. position plot, depending upon design requirements, cost, and complexity.

An IR sensing PIN code shown in FIG. 9, with appropriate circuitry, may be substituted for the photo-transistor shown in FIG. 6, in order to obtain a wider operating band-width. The circuit, shown in FIG. 9, provides usable signal band-width to 200 MHz. It appears that Signal-to-Noise Ratio is better at the higher RF frequencies.

In compliance with the statute, the invention described herein has been described in language more or less specific as to structural features. It should be understood however, that the invention is not limited to the specific features shown, since the means and construction shown, is comprised only of the preferred embodiments for putting the invention into effect. The invention is therefore claimed in any of its forms or modifications within the legitimate and valid scope of the amended claims, appropriately interpreted in accordance with the doctrine of equivalents.

We claim:

1. An ion acoustic remote substance identification and location system, comprising:
 a. an ion acoustic voltage radiation source;
 b. means for ionizing an intermediate chemical to produce a probing signal of a desired frequency and amplitude capable of propagating a voltage from said ion acoustic voltage radiation source to a desired target substance to produce non-destructive molecular resonance therein;

c. means to transmit said voltage and said probing signal to a target substance to cause said target substance to undergo molecular resonance and produce a characteristic electrical response signal;

d. an IR detector for detecting said electrical response signal from said target substance, said IR detector includes one or more infrared emitters that produce a beam of IR radiation that is transmitted to a target substance, said outer housing also including an electrode used to detect a response signal from said target substance;

e. a transformer assembly attached to said electrode, said transform assembly includes a metallic outer housing;

f. an artificial grounding device connected to said IR detector and said transformer assembly, said artificial grounding device includes an IR emitter diode that produces a IR signal when a current is applied thereto, said artificial grounding device also including an opaque, insulative shield that is slightly smaller than said outer housing thereby creating a gap through which said IR signal from said IR emitter diode may be transmit to ionize the air; and, g. means to identify said target substance based on said electrical response signal detected by said IR detector.

* * * * *